United States Patent
Kaufman

(10) Patent No.: US 8,672,910 B1
(45) Date of Patent: Mar. 18, 2014

(54) MALE INCONTINENCE AID

(71) Applicant: Kenneth M. Kaufman, Skaneateles, NY (US)

(72) Inventor: Kenneth M. Kaufman, Skaneateles, NY (US)

(*) Notice: Subject to any disclaimer, the term of this patent is extended or adjusted under 35 U.S.C. 154(b) by 0 days.

(21) Appl. No.: 13/759,381

(22) Filed: Feb. 5, 2013

(51) Int. Cl.
*A61F 5/44* (2006.01)
*A61F 5/30* (2006.01)
*A61F 6/02* (2006.01)
*A61F 2/00* (2006.01)
*A61F 13/14* (2006.01)
*A61F 5/24* (2006.01)
*A61F 13/00* (2006.01)

(52) U.S. Cl.
CPC ... *A61F 5/30* (2013.01); *A61F 6/02* (2013.01); *A61F 2/005* (2013.01); *A61F 2013/00174* (2013.01); *A61F 2/0031* (2013.01); *A61F 13/148* (2013.01); *A61F 2/0009* (2013.01); *A61F 5/24* (2013.01); *Y10S 128/25* (2013.01)
USPC .... 604/349; 604/331; 128/98.1; 128/DIG. 25

(58) Field of Classification Search
CPC ............. A61F 6/02; A61F 2/005; A61F 5/30; A61F 2013/00174; A61F 2/0031; A61F 13/148; A61F 2/0009; A61F 5/24; Y10S 128/25
USPC .................................. 604/331, 349; 128/98.1
See application file for complete search history.

(56) References Cited

U.S. PATENT DOCUMENTS

| | | | |
|---|---|---|---|
| 655,618 A | 8/1900 | Garvey | |
| 1,581,009 A | 4/1926 | McSherry | |
| 1,768,397 A | 6/1930 | Courtney | |
| 2,468,348 A | 4/1949 | Shore | |
| 2,559,762 A | 7/1951 | Furr | |
| 2,615,445 A | 10/1952 | Holmes | |
| 2,713,340 A | 7/1955 | Meminger | |
| 3,080,865 A | 3/1963 | Vincent | |
| 3,787,892 A * | 1/1974 | Quinn | 2/466 |
| 4,569,465 A * | 2/1986 | O'Farrell | 224/660 |
| 5,122,111 A * | 6/1992 | Sebastian et al. | 602/19 |
| 5,131,386 A | 7/1992 | Simmons | |
| 5,177,814 A * | 1/1993 | Courtney | 2/326 |
| 5,439,007 A | 8/1995 | Fischer | |
| 5,727,568 A | 3/1998 | Kiser | |
| 6,270,469 B1 | 8/2001 | Mott | |
| D480,812 S | 10/2003 | Moore-Steele | |
| 8,365,737 B2 * | 2/2013 | Mitsui et al. | 128/830 |

* cited by examiner

Primary Examiner — Tatyana Zalukaeva
Assistant Examiner — Andrew J Mensh
(74) Attorney, Agent, or Firm — Bernhard P. Molldrem, Jr.

(57) ABSTRACT

An external urinary incontinence aid in the form of a pelvic floor support sling has three components. A belt or girdle encircles the patient at or above the waist. An X-shaped elastic cross strap has hook/loop fastener strips at its ends to attach removably to the outer surface of the girdle, and hook/loop material at the crossing or intersection. A pressure block or pad is attached removably to the crossing portion of the cross strap, and presses against the perineum or pelvic floor, applying pressure to occlude the urethra and prevent or reduce involuntary leakage.

20 Claims, 2 Drawing Sheets

MALE INCONTINENCE AID

FIELD OF THE INVENTION

The present invention relates to male incontinence aids to be worn externally and which provide assistance to a male patient in restricting or blocking the involuntary flow of urine through the patient's urethra. The invention is more specifically directed to a non-invasive control for male incontinence that does not involve chemical intervention, surgery, catheters or mechanical clamps, and can be donned and doffed at will, that is, applied and removed when the patient so desires, and is infinitely adjustable for fit, comfort, and effectiveness. In particular, the invention is directed to urinary control devices that exert a gentle, but firm pressure on the urethra externally from underneath the pelvic floor, that is, at the perineum, to assist the sphincter muscles that are normally responsible for controlling urine flow, but which may have become weakened for any of a variety of reasons, such as age, surgery, accident, infection, or disease.

BACKGROUND OF THE INVENTION

A number of appliances have been proposed to assist the control of urine flow in men whose urinary sphincter muscles may have become weakened or in whom the associated nerves may have been damaged, resulting in involuntary flow of the urine, from small leakage to significant flow. The non-surgical external appliances have included, e.g., penis clamps which apply a closing pressure to the portion of the urethra that extends through the penis. These devices can be uncomfortable for the wearer, and require manipulation to release the external pressure so that the wearer can void his bladder. Also, the wearing of this type of aid can result in necrosis of tissues around the area where the penis clamp is worn and can result in urinary tract infections if worn for extended durations. An alternative incontinence aid is described in Vincent U.S. Pat. No. 3,080,865. That device involves an inflatable balloon that is to be worn on a spring member so that the balloon applies some pressure against the patient's perineum. However the device is cumbersome, and is difficult to install and remove. Another alternative incontinence aid is described in Kiser U.S. Pat. No. 5,727,568, involving a rigid block that is pressed against a narrow portion of the patient's penis to apply closing pressure to the urethra without applying pressure to other tissues. The device can be uncomfortable to wear and has to be custom made to fit the individual patient. The device requires straps that pass in the front of the patient's lower abdomen to hold the rigid pressure block, and the patient's penis, at a fixed location. Some patients require special underwear to hold the device properly in place.

OBJECTS AND SUMMARY OF THE INVENTION

It is an object of the present invention to provide a simple, straightforward external incontinence aid that is reliable and comfortable to wear.

It is another object to provide a male incontinence aid that the patient or wearer can put on easily and which can be easily removed when not needed.

It is a further object to provide an incontinence aid that allows the wearer to apply pressure to the perineal area when needed to prevent involuntary flow of urine, and which allows the wearer to easily relieve the pressure on the perineum so that he can urinate when desired or needed.

It is a further object to provide an incontinence aid that permits the pressure that is applied to the perineum to be adjusted by the wearer.

In accordance with an aspect of the present invention, the male incontinence aid has a belt or girdle encircling the patient's abdomen, approximately at the waist. On its internal surface this may favorably be formed of a breathable elastomeric material, such as a neoprene rubber. On its external surface, at least some portions are constituted as a hook/loop fastener material, e.g. Velcro®. In practice, the outer surface of the girdle serves as the velour or loop fastener material, and the inner surface provides a frictional resistance against the wearer's skin. An elastic cross strap is formed of elastic web members that intersect to form an "X" shape, so that the cross strap has a central crossing portion and a plurality of strap ends. The crossing portion has hook/loop fastener material attached to it, favorably the loop type material, while the ends have hook/loop fastener material affixed to them, favorably strips of the hook type material. The cross strap is adapted to be worn by the patient with the ends attached removably to the exterior of the girdle and with the crossing portion thereof adjacent the pelvic floor of the patient. A wedge-shaped pressure block member is provided, and in some cases a plurality of block members are provided. These pressure block members are formed of a durable rigid or semi-rigid material, e.g., wood, plastic resin, or dense foam. Each block member has a base (wide) side on which a portion of the hook/loop fastener material is affixed, e.g., cemented. In this example, this can be the hook type material, so that the block may be removably attached to the crossing portion of the elastic cross strap. When the incontinence aid is worn, the upper (narrow) part of the block member that is attached to the crossing portion bears against the perineum of the patient at the patient's pelvic floor and is urged against the perineum by the elasticity of the cross strap. The ends of the cross-strap can be adjusted by their placement on the girdle to apply the appropriate force so that the pressure block prevents involuntary flow, but also so that the block causes no discomfort.

A number of these pressure block members may be provided, with the block members being of different dimensions so that the patient can choose one of the block members of the size that best suits the patient's needs for urinary flow restriction and wearing comfort, and can attach that one to the crossing portion of said cross strap.

The device of this invention can be considered an external pelvic floor support sling, intended to reduce or prevent urinary incontinence in men. Unlike other methods or treatments for male incontinence, the device does not involve drugs, surgery, clamps, catheters or any other method that must be prescribed, applied or implanted by a physician. The device is entirely non-invasive and external, can be removed at will, and is infinitely adjustable for fit, comfort and effectiveness. The principle of operation is to exert an upward, concentrated force, or pressure, on the pelvic floor, i.e., perineum, that is, on the area between the back of the scrotum and the anus. This force or pressure helps compress or occlude the urethra, thereby reducing, restricting, or preventing the involuntary flow of urine. The amount of force applied is limited, so there is little if any discomfort from wearing the device, and little or no risk of tissue damage.

The device is intended to be worn outside the man's underpants or briefs, and underneath his trousers. The device is not visible when worn, and does not restrict freedom of movement. The device can be worn when walking, running, or cycling, for example. Because the device is worn outside the underwear, the device does not readily become soiled. The components are made of durable materials, and can be cleaned by hand-washing in warm soapy water, and then air-dried.

The main aspects of the invention will become apparent from the ensuing description of a preferred embodiment, given in connection with the accompany Drawing figures. One embodiment will be described, but it should be appreciated that many variations of this male incontinence aid are possible.

DETAILED DESCRIPTION OF THE PRESENT INVENTION

Figure 1:
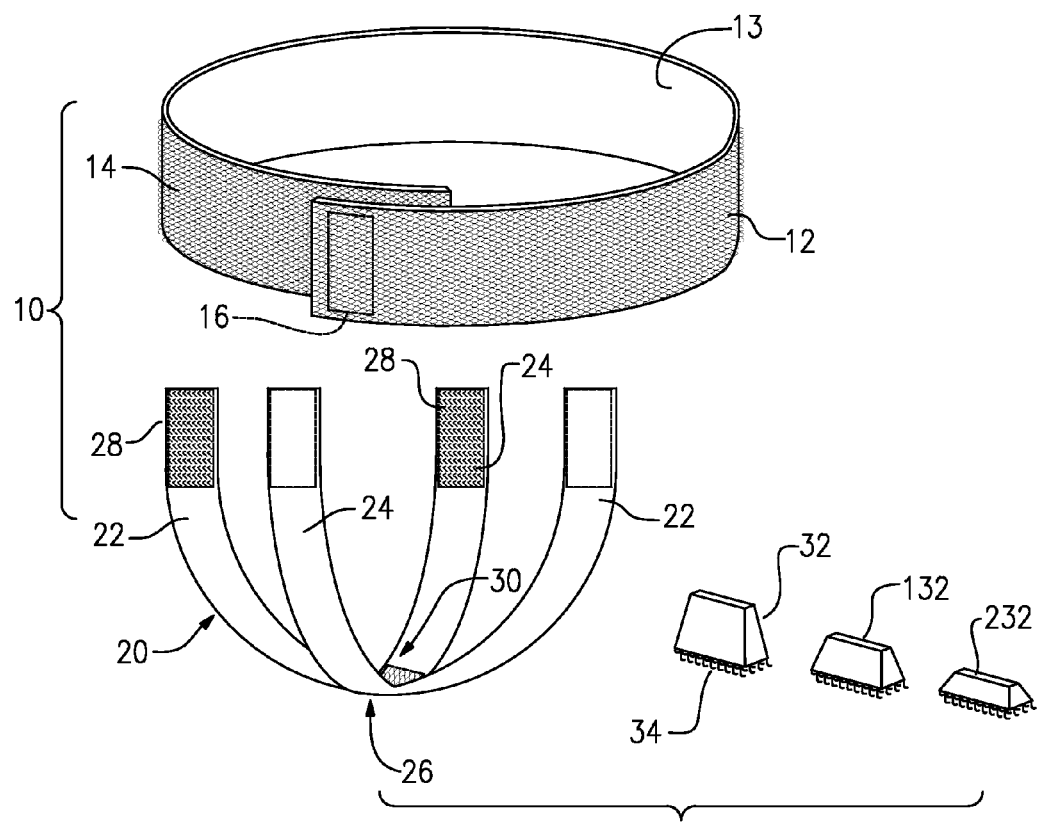
FIG. 1 is an exploded view showing the components of the incontinence aid according to one embodiment of this invention.
Figure 2:
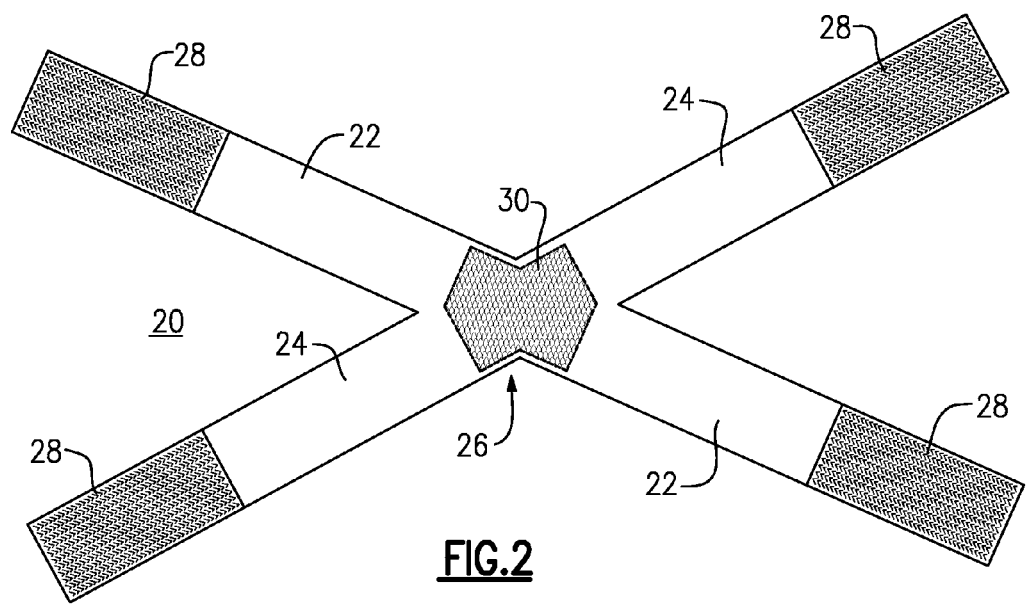
FIG. 2 is a plan view of the cross strap of this embodiment.

Referring now to FIGS. 1 and 2 of the Drawing, a male incontinence aid 10 according to one preferred embodiment is shown as an assembly or kit, with a girdle, cinch, or belt 12 formed of an elastic material, preferably also a breathable material that allows ventilation of heat and moisture. The interior surface 13 thereof, that is, the side worn against the skin, is a rubber-like material, such as neoprene, that provides a frictional resistance to the downward pull of the cross strap 20. The exterior surface 14, that is the side worn to the outside, is a napped polyester or similar fabric that serves as the "loop" component of a hook-and-loop fastening system (e.g., Velcro®), and will securely engage the hook portion of the hook-and-loop system. Favorably, the girdle 12 is a nominal six-inches (15 cm) wide, and of a soft, flexible material that can be comfortably worn over the subject's abdomen at or just above the waist. There is a strip of hook-type material 16 sewn at one end on the inside surface 13, to engage the outer surface 14 when the belt or girdle is being worn, and which can be placed anywhere on the outer surface 14 to adjust for fit and comfort. The function of the girdle is to support a cross strap or sling 20 that passes under and against the subject's perineum. The girdle 12 is worn wrapped snugly around the waist, with the top of the band approximately at the lower end of the subject's rib cage.

The cross strap or sling 20 is formed of first and second elastic web bands 22 and 24, each of a nominal 1.5 inches (6 cm) in width and about twenty-four inches (60 cm) in length. These are joined and sewn together at the middle to form an "X" shape, thus defining a central crossing portion 26. The acute angle of the cross strap in this embodiment is a nominal fifty degrees. At each free end of the straps or bands 22, 24 there is a strip 28 of hook-type fastener material, intended to engage the outer surface 14 of the girdle 12. The strips 28 may be a nominal four inches (10 cm) in length. A small patch of loop-type fastener material 30 is sewn at the central crossing portion 26 of the cross strap 20. When the device is being worn, the cross-strap 20 is positioned with the intersection or crossing portion 26 at the wearer's perineum and with the end fastener material strips 28 secured to the outer surface of the girdle 12. The web bands 22 and 24 can be adjusted so as to apply a firm upward force against the perineum.

One or more pressure blocks 32 are provided, being about one half inch to an inch (2.5 cm) thick, with a narrow upper contact area or ridge portion designed to bear against the wearer's perineum and with a wider lower or base surface on which there is affixed a patch of a hook-type fastener material 34. Tapered side walls extend from the base surface to the upper ridge portion. In this embodiment, the incontinence aid 10 includes several similar pressure blocks, 32, 132, 232, of different dimensions, so that the patient can select one that best fits his needs for stoppage of involuntary urine flow and for comfort. Each of these has a fastener material attached to the base as described. The pressure block 32 can be wood or a rigid, durable plastic resin material, or may be a semi-rigid material such as dense, closed-cell foam, and should be washable and capable of being sanitized.

The pressure block 32 is attached onto the crossing portion 26 of the cross strap 20, with the hook material 34 engaging the loop material 30 of the cross strap. This positions the block 32 so that its upper contact surface or ridge portion bears on the patient's perineum, in the area immediately behind the scrotum. When this device is worn, the straps or web bands 22 and 24 of the cross strap 20 are adjusted to provide upward force, to press the pressure block 32 upwards against the perineum, thereby applying the pressure necessary to occlude the urethra and prevent or reduce the involuntary flow or leakage of urine.

When the wearer needs to evacuate his bladder, it is not necessary to remove the device or any of its parts. It is only necessary to open the girdle 12 by disengaging the hook material 16 from the exterior surface 14 of the girdle, and by pulling the two ends of the girdle 12 aside, with the cross-strap ends still attached. Then the user pulls down the front of his underpants 36. This releases the upward force on the pressure block member 32, permitting normal urination. When done, the wearer simply pulls the front of the underpants back up and re-positions the girdle 12 and secures it with the hook material 16, which automatically re-establishes the upward force on the pressure block 32.

Figures 3, 4:
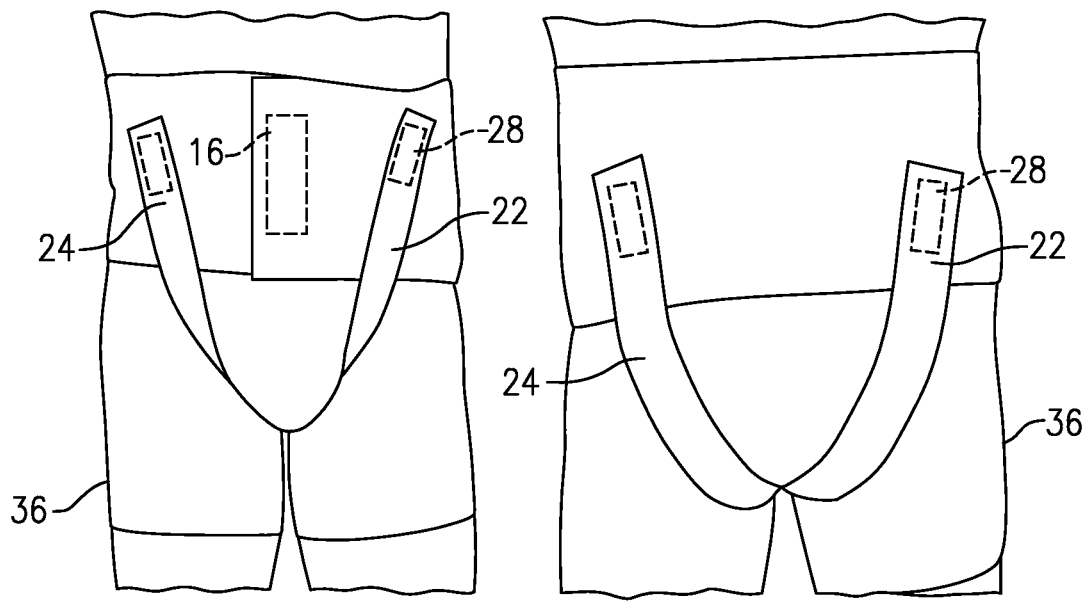
FIG. 3 is a front view of this embodiment as worn by a male patient.
FIG. 4 is a rear view thereof.
Figure 5:
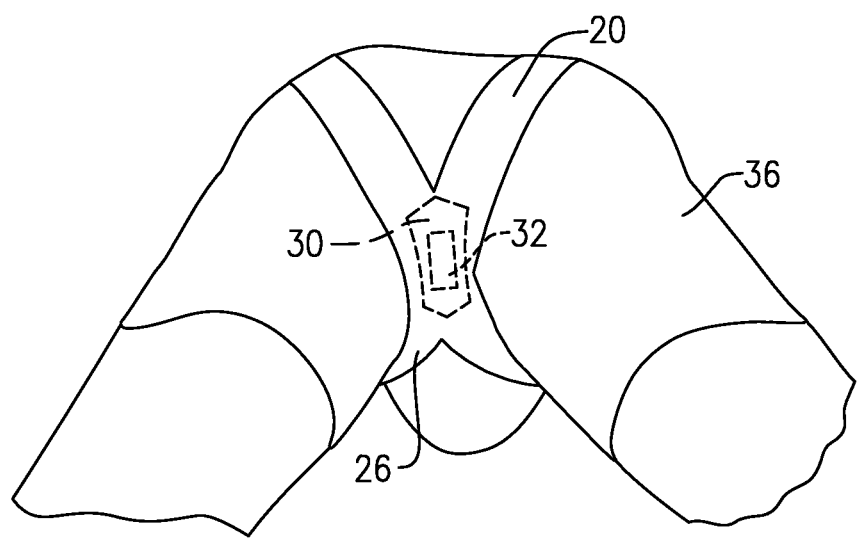
FIG. 5 is a bottom view thereof.

The wearer applies the incontinence device 10 outside his underwear, e.g., over his undershorts or briefs 36, as shown in FIGS. 3, 4 and 5, with the girdle 12 secured in place at or just above the waist. The cross strap 20 is then suspended from the girdle 12 with the ends of the web members 22 and 24 passing around the wearer's scrotum to the front side and then over the wearer's buttocks to the back side, with the crossing portion 26 being situated just behind the scrotal area, as shown in FIG. 5.

After having been worn, the cross strap 20 and the pressure block 32 can be rinsed and then washed in warm, soapy water, and air dried. The pressure block 32 and the cross strap 20 do not contact the wearer directly, as they are worn outside the wearer's undergarments. Because the device does not contact the wearer, and is non-invasive, the device can be obtained and employed without a prescription in most jurisdictions.

The cinch or girdle portion of this incontinence aid can be constructed of a neoprene material on its interior surface, favorably with openings to provide for ventilation, and a stretch fabric with a layer of a polyester loop material affixed on all or portions of its outer surface. In another embodiment, the girdle may be provided with mesh panels for ventilation. The cross strap portion need not be of the same dimensions and configuration as shown in this preferred embodiment, and a wide variety of materials may be employed in its construction.

The foregoing description and drawings present an embodiment of this invention for the purpose of explaining the invention. However, the invention is not limited to the disclosed embodiment, but rather many modifications and variations thereof would present themselves to persons skilled in the art without departing from the scope and spirit of the invention as defined in the appended Claims.

I claim:

1. A male incontinence aid to be worn by a male patient to impose a pressure against a perineum of the patient at a pelvic floor of the patient, comprising in combination an elastic flexible girdle encircling the patient's waist and having an internal surface and an external surface, at least portions of the external surface being covered with a hook/loop fastener material, and at least portions of the interior surface of said girdle being formed of a neoprene rubber;

an elastic cross strap formed of a pair of crossing elastic flexible web members and being joined together at a central crossing portion and each said web member having two ends, with said crossing portion and said ends having said hook/loop fastener material affixed thereon; and being adapted to be worn by the patient with said ends attached removably to the external surface of said girdle and with the crossing portion thereof adjacent the pelvic floor of the patient; and a rigid block member formed of a rigid or material having a wedge shape with a narrower upper side ridge portion adapted to contact against a portion of the patient's perineum where the patient's urethra is located, a wider base side on which a portion of said hook/loop fastener material is affixed, and tapered side portions leading from the base side to the upper side ridge portion, the base side being adapted to be removably and adjustably attached to the crossing portion of the elastic cross strap such that when the incontinence aid is worn the narrower upper side ridge portion of the block member is urged against the perineum by the elasticity of the cross strap and bears against the perineum of the patient at the patient's pelvic floor to concentrate the force of the elastic cross strap against the wearer's urethra and to assist in occluding the wearer's urethra.

2. The male incontinence aid according to claim 1 in which the hook/loop fastener material on said girdle is a loop material and the hook/loop material affixed onto said ends of said cross strap is a hook material.

3. The male incontinence aid according to claim 1 wherein the hook/loop fastener material that is affixed onto the crossing portion of said elastic cross strap is a loop material.

4. The male incontinence aid according to claim 1 wherein the internal surface of said girdle is formed of a neoprene rubber.

5. A male incontinence aid to be worn by a male patient to impose a pressure against a perineum of the patient at a pelvic floor of the patient, comprising in combination a flexible elastic girdle encircling the patient's waist and having an interior surface and an external surface, at least portions of the external surface being covered with a hook/loop fastener material, and at least portions of the interior surface of said girdle being formed of a neoprene rubber;

an elastic cross strap formed of a pair of crossing elastic flexible web members and being joined together at a central crossing portion and each of said elastic flexible web member having two ends, with said crossing portion and said ends having said hook/loop fastener material affixed thereon; and being adapted to be worn by the patient with said ends attached removably to the external surface of said girdle and with the crossing portion thereof adjacent the pelvic floor of the patient; and a plurality of rigid block members, each being formed of a rigid material and each having a narrower upper side ridge portion adapted to contact against a portion of the patient's perineum where the patient's urethra is located, a wider base side on which a portion of said hook/loop fastener material is affixed, and tapered side portions leading from the base side to the upper side ridge portion, the base side and said portion of hook/loop material being adapted to be removably attached to the crossing portion of the elastic cross strap such that when the incontinence aid is worn a selected one of the block members is removably and adjustably attached to said crossing portion and the narrower upper side ridge portion thereof is urged against the perineum by the elasticity of the cross strap and bears against the perineum of the patient at the patient's pelvic floor to press against the wearer's urethra and assist in occluding the wearer's urethra.

6. The male incontinence aid according to claim 5 wherein the hook/loop fastener material that is affixed onto the crossing portion of said elastic cross strap is a loop material.

7. The male incontinence aid according to claim 5 wherein the hook/loop fastener material that is affixed onto the crossing portion of said elastic cross strap is a hook material.

8. The male incontinence aid according to claim 5 wherein the respective block members of said plurality of block members are of different dimensions so that the patient can choose one of the block members, as best suits the patient's needs for urinary flow restriction and wearing comfort, to attach to the crossing portion of said cross strap.

9. The male incontinence aid according to claim 5 wherein said girdle is formed of an elastomeric, breathable material.

10. The male incontinence aid according to claim 5 wherein the interior surface of said girdle is formed of a neoprene rubber.

11. The male incontinence aid according to claim 1, wherein said male patient is provided with an undergarment covering the region of his pelvic floor and perineum, and wherein said cross strap and said block member are worn outside said undergarment.

12. The male incontinence aid according to claim 1, wherein the pressure imposed by said block member against the perineum of the patient is adjustable by removing and replacing the ends of said cross strap on the external surface of said girdle.

13. The male incontinence aid according to claim 5, wherein said male patient is provided with an undergarment covering the region of his pelvic floor and perineum, and wherein said cross strap and said block member are worn outside said undergarment.

14. The male incontinence aid according to claim 5, wherein the pressure imposed by said block member against the perineum of the patient is adjustable by removing and replacing the ends of said cross strap on the external surface of said girdle.

15. The male incontinence aid according to claim 1, wherein said block member is adapted such that only said upper side ridge portion thereof presses against the perineum of the patient.

16. The male incontinence aid according to claim 5, wherein each said block member is adapted such that only said upper side ridge portion thereof presses against the perineum of the patient.

17. The male incontinence aid according to claim 1, wherein the interior surface of said flexible elastic girdle is adapted to provide sufficient frictional resistance against the skin of the patient at or above the patient's waist to resist downward pull of said elastic cross strap.

18. The male incontinence aid according to claim 5, wherein the interior surface of said flexible elastic girdle is adapted to provide sufficient frictional resistance against the skin of the patient at or above the patient's waist to resist downward pull of said elastic cross strap.

19. The male incontinence aid according to claim 1, wherein said flexible elastic girdle has a nominal width of six inches.

20. The male incontinence aid according to claim 5, wherein said flexible elastic girdle has a nominal width of six inches.

* * * * *

UNITED STATES PATENT AND TRADEMARK OFFICE
CERTIFICATE OF CORRECTION

| | | |
|---|---|---|
| PATENT NO. | : 8,672,910 B1 | Page 1 of 1 |
| APPLICATION NO. | : 13/759381 | |
| DATED | : March 18, 2014 | |
| INVENTOR(S) | : Kaufman | |

It is certified that error appears in the above-identified patent and that said Letters Patent is hereby corrected as shown below:

In the Claims

Col. 5, Claim 1, line 22 should read:
A rigid block member formed of a rigid material having Col. 5, Claim 5, line 60 should read:
Web members having two ends, with said crossing por- Signed and Sealed this
Thirteenth Day of January, 2015

Michelle K. Lee
*Deputy Director of the United States Patent and Trademark Office*